United States Patent [19]
Yoneda et al.

[11] Patent Number: 5,932,015
[45] Date of Patent: Aug. 3, 1999

[54] PROCESS FOR MANUFACTURING CRYSTALLINE MALTITOL AND CRYSTALLINE MIXTURE SOLID CONTAINING THE SAME

[75] Inventors: Susumu Yoneda; Yoshiaki Tateno; Mitsuo Magara, all of Shizuoka; Naoki Okamoto, Chiba, all of Japan

[73] Assignee: Towa Chemical Industry Co., Ltd., Tokyo, Japan

[21] Appl. No.: 08/888,138

[22] Filed: Jul. 3, 1997

[30] Foreign Application Priority Data

Jul. 5, 1996 [JP] Japan ................................. 8-194099

[51] Int. Cl.$^6$ ................................................. C13D 3/14
[52] U.S. Cl. ........................... 127/36; 127/40; 127/46.2
[58] Field of Search ............................... 127/36, 40, 46.2

[56] References Cited

U.S. PATENT DOCUMENTS

| | | | |
|---|---|---|---|
| 4,422,881 | 12/1983 | Devos et al. | 127/46.1 |
| 4,846,139 | 7/1989 | Devos et al. | 127/36 |
| 4,849,023 | 7/1989 | Devos et al. | 127/36 |

*Primary Examiner*—David Brunsman
*Attorney, Agent, or Firm*—Smith, Gambrell & Russell, LLP; Beveridge, DeGrandi, Weilacher & Young Intellectual Property Group

[57] ABSTRACT

Provides an economical method for manufacturing high-value added crystalline maltitol and crystalline mixture solid containing this by means of a process wherein a syrup with a maltose content of 40 to 75% by weight in the solid component is subjected to catalytic hydrogenation, the sugar alcohol syrup is then subjected to chromatographic separation to produce a maltitol-containing syrup fraction with a high maltitol content in the solid component, and the maltitol-containing syrup fraction is then subjected to chromatographic separation.

6 Claims, 3 Drawing Sheets

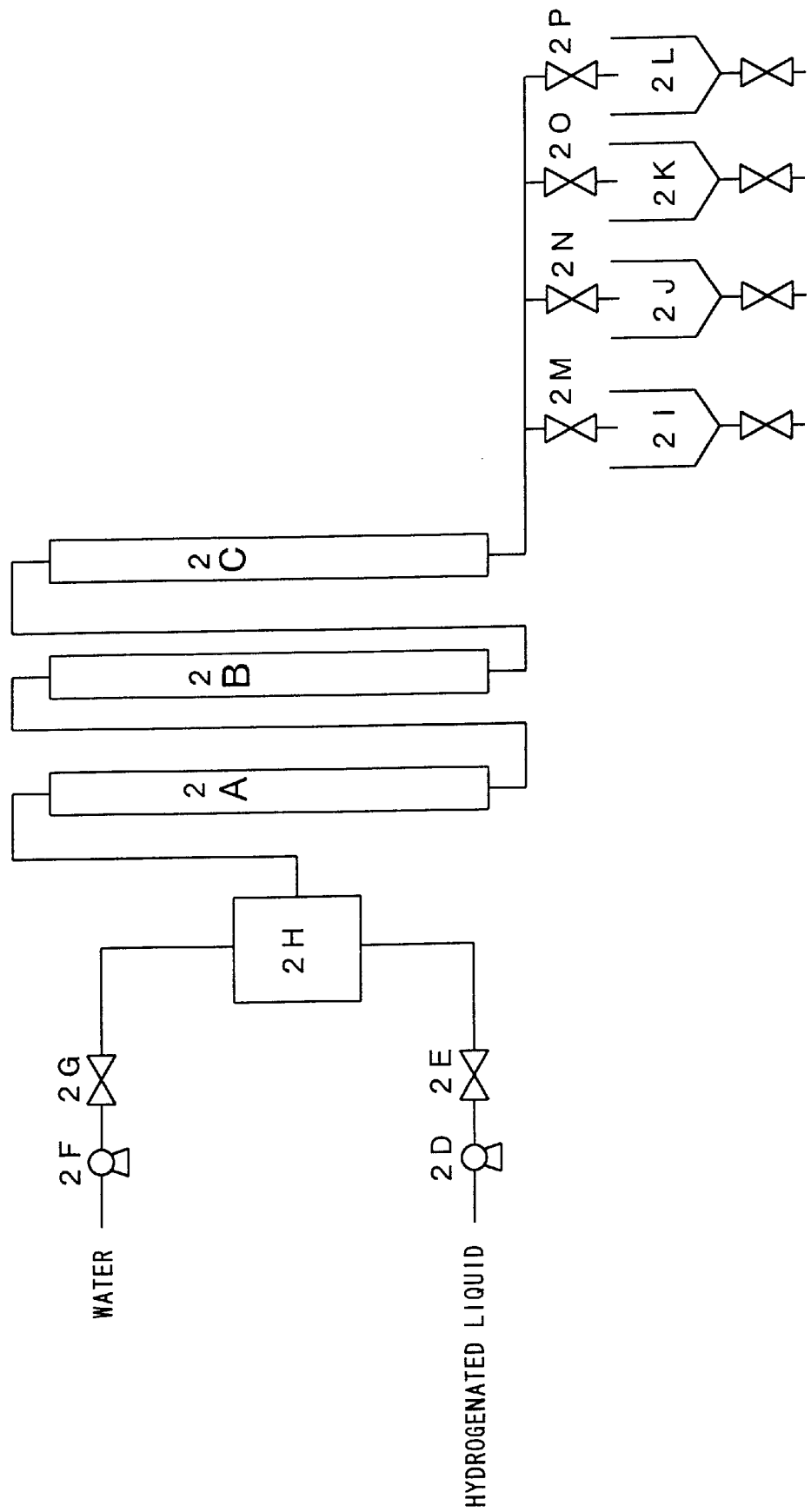

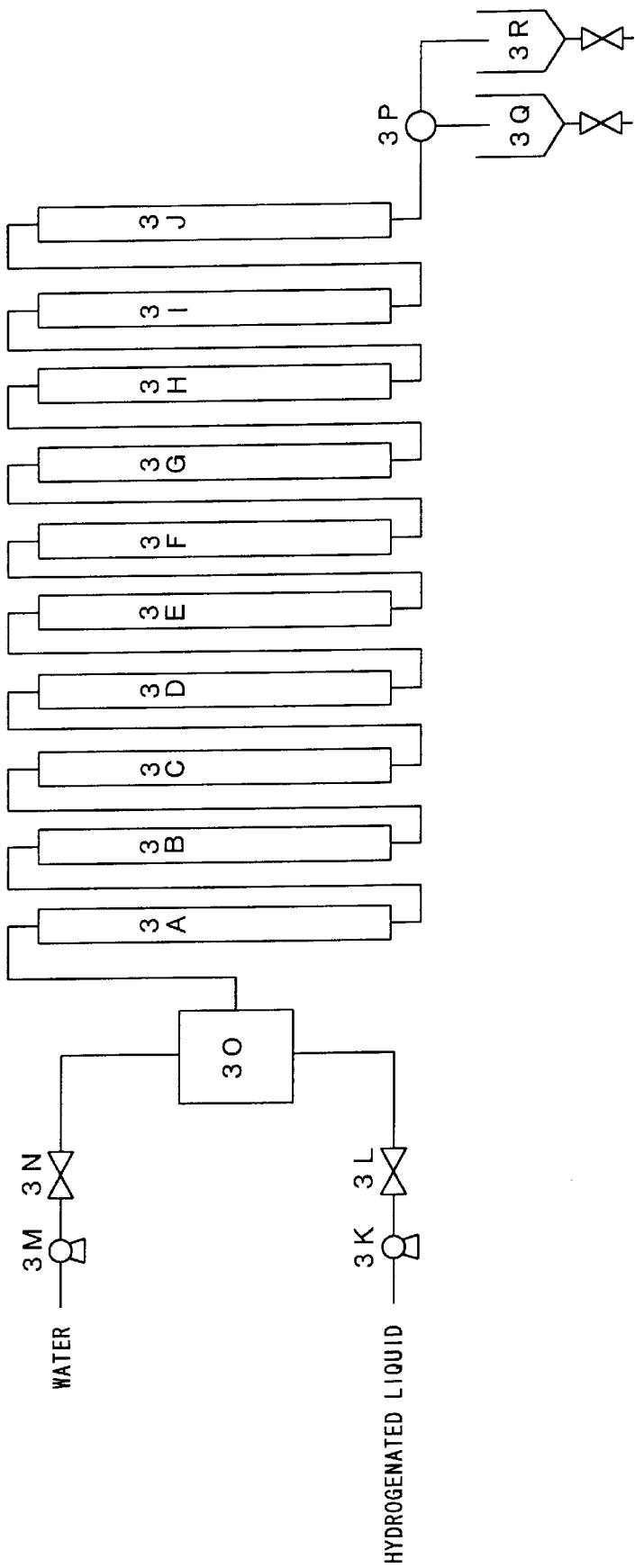

PROCESS FOR MANUFACTURING CRYSTALLINE MALTITOL AND CRYSTALLINE MIXTURE SOLID CONTAINING THE SAME

TECHNICAL FIELD

The present invention relates to a process for manufacturing crystalline maltitol and crystalline mixture solid containing this, and more particularly to a process for manufacturing in any desired ratio both crystalline maltitol and crystalline mixture solid containing this, using the same raw materials.

BACKGROUND ART

Maltitol is a sugar alcohol obtained through catalytic hydrogenation of maltose. Its sweet taste and degree of sweetness are similar to those of sucrose, and since it is hardly utilized by oral bacteria, it does not cause a tooth decay. It is hardly digested by human digestive enzymes, is stable against the heat, and does not promote insulin secretion. It also has a beneficial effect on the absorption of various minerals, and other desirable functions.

Crystalline maltitol and crystalline mixture solid containing it are widely used as materials in foods, pharmaceuticals, and cosmetics due to their low hygroscopicity and excellent performance as an excipient.

Method for manufacturing crystalline maltitol is disclosed in (1) Japanese TOKKYO-KOKAI-KOHO (18-month Publication of Unexamined Patent Application) SHOWA 57(1982)-134498 (hereinafter referred to as TOKKAISHO 57134498),(2) Japanese TOKKYO-KOKOKU-KOHO (Publication after Examination for Opposition) HEISEI 2(1990)-11599 (hereinafter referred to as TOKKOHEI 2-11599), and (3) Japanese TOKKYO-KOKAI-KOHO (18-month Publication of Unexamined Patent Application) SHOWA 61(1986)-180795 (hereinafter referred to as TOKKAISHO 61-180795).

In the method in (1), an underground starch such as potato starch is liquefied, saccharified, purified, and the maltose crystallized in order to prepare high-purity maltose with a solids maltose content of 93 to 100% by weight in the solid component. This product is then subjected to catalytic hydrogenation to convert it to high-purity maltitol, which is then crystallized to manufacture crystalline maltitol.

In the method in (2), maltose syrup with a maltose content of 50 to 80% by weight in the solid component is subjected to catalytic hydrogenation to convert it to the corresponding maltitol syrup, which is then subjected to chromatographic separation to obtain a fraction with a maltitol content of 87% by weight or more in the solid component. This is concentrated and crystallized to manufacture crystalline maltitol.

In the method in (3), maltose syrup with a maltose content of 50% by weight or more in the solid component is subjected to catalytic hydrogenation, and then subjected to chromatographic separation to simultaneously obtain (i) a fraction which has maltitol as its principal component and which is useful as a raw material for the manufacture of crystalline maltitol and crystalline mixture solid containing this, and (ii) a fraction having maltotriitol as its principal component.

(1) above also discloses methods for manufacturing crystalline mixture solid containing crystalline maltitol using known methods such as block grinding method, fluidized granulation, and spray drying from a maltitol massecuite.

However, these conventional methods have numerous problems and are not satisfactory as methods for the manufacture on an industrial scale of crystalline maltitol and crystalline mixture solid containing this.

For example, in the manufacturing method in (1), in the step of liquefying starch a solution having a low DE (dextrose equivalent) needs to be preliminary produced to be saccharified in order to prepare high-purity maltose. In the usual concentration, the liquid has an extremely high viscosity, so it is necessary to conduct liquefaction and saccharification at low concentrations. This requires that large volumes of water be evaporated during the concentration process, and that large amounts of enzymes be used during saccharification. It is also necessary to use isoamylase, which is expensive.

Further, in order to maintain maltitol purity during catalytic hydrogenation, it is necessary to conduct the process while using large quantities of catalyst under mild temperature conditions in order to prevent decomposition of the maltose and maltitol. This is disadvantageous from an economic standpoint.

With the method in (1), the limit of the purity of the maltose obtainable through saccharification is usually about 90 to 93%, and, accordingly, the large quantities of mother liquor produced through crystallization of the maltitol obtained by catalytic hydrogenation have a low maltitol content, making it difficult to recrystallize maltitol from the mother liquor, or to manufacture crystalline mixture solid containing this. Accordingly, the method produces large amounts of a mother liquor which is suitable only for use as liquid products, such as hydrogenated maltose syrup, hydrogenated starch hydrolysates and the like having a lower added value than crystalline maltitol.

With the manufacturing methods in (2) and (3), the syrup containing maltose of about 50 to 80% by weight, which is ordinarily used as the raw material, also contains large quantities of glucose and oligosaccharide. Accordingly, after completing catalytic dehydrogenation, when it is attempted to obtain a maltitol fraction of high purity in a single chromatographic separation, the recovery rate, that is, productivity, is poor; conversely, when it is attempted to raise productivity, the maltitol content of the fractionated liquid declines, making it difficult to ultimately crystallize the maltitol.

Particularly with the method in (2), since the mother liquor separated in crystallization is returned to the chromatographic separation process in order to raise crystalline maltitol productivity, an oligosaccharide fraction whose DP is 3 or more, a product with virtually no utility value, is ultimately produced in the chromatographic separation process.

With the method in (2), when the mother liquor is returned to the chromatographic separation process, the sugar composition of the mother liquor is significantly affected by the outcome of starch saccharification and the condition of crystallization of the crystalline maltitol, so a rather complex operating management is required to obtain fractions of a certain maltitol purity during the chromatographic separation process.

With the method in (1), even where crystalline mixture solid containing crystalline maltitol are manufactured using such common methods as block grinding method, fluidized granulation, and spray drying from a maltitol massecuite, the economic disadvantages of the method are already apparent at the maltose preparation stage.

With the foregoing in view, it is an object of the present invention to overcome the problems outlined above to provide a method for the economical manufacture of high-value added crystalline maltitol and crystalline mixture solid containing this.

SUMMARY OF THE INVENTION

As a result of painstaking research conducted with the purpose of overcoming the aforementioned problems, the inventors succeeded in developing a method for the extremely economical manufacture of high-value added crystalline maltitol and crystalline mixture solid containing this, which involves subjecting a syrup with a maltose content of 40 to 75% by weight in the solid component, an inexpensively procured product, to catalytic hydrogenation under the conditions described below, and then to a two-stage chromatographic separation process.

The means used in the invention to solve these problems are as follows.

Firstly a process for manufacturing crystalline maltitol and crystalline mixture solid containing the maltitol, characterized in that the process passes sequentially through the following steps:

1) the first step of hydrogenating syrup having a maltose content of 40 to 75% by weight in the solid component under the existence of catalyst to obtain corresponding syrup of sugar alcohol;
2) the second step of chromatographically separating said syrup of sugar alcohol by supplying said syrup of sugar alcohol to a column packed with a cation exchange resin to obtain high sorbitol content fraction, maltitol syrup fraction (a) having a maltitol content of 80.5 to 86.5% by weight in the solid component and polyol fraction whose degree of polymerization (DP) is 3 or more;
3) the third step of chromatographically separating said maltitol syrup fraction (a) by supplying said maltitol syrup fraction (a) to a column packed with a cation exchange resin to obtain high sorbitol content fraction, maltitol syrup fraction (b) having a maltitol content of 97.5% by weight or more in the solid component and polyol fraction whose degree of polymerization (DP) is 3 or more;
4) the fourth step of crystallizing after a concentration of said maltitol syrup fraction (b) and separating crystalline maltitol from mother liquor having a maltitol content of 90% by weight or more in the solid component, and
5) the fifth step of spray-drying or kneading under cooling the mother liquor obtained in the fourth step in the presence of a seed crystal to obtain crystalline mixture solid containing crystalline maltitol.

Secondly a process for manufacturing crystalline maltitol and crystalline mixture solid containing the maltitol, characterized in that the process passes sequentially through the following steps:

1) the first step of hydrogenating syrup having a maltose content of 40 to 75% by weight in the solid component under the existence of catalyst to obtain corresponding syrup of sugar alcohol;
2) the second step of chromatographically separating said syrup of sugar alcohol by supplying said syrup of sugar alcohol to a column packed with a cation exchange resin to obtain high sorbitol content fraction, maltitol syrup fraction (a) having a maltitol content of 80.5 to 86.5% by weight in the solid component and polyol fraction whose degree of polymerization (DP) is 3 or more;
3) the third step of chromatographically separating said maltitol syrup fraction (a) by supplying said maltitol syrup fraction (a) to a column packed with a cation exchange resin to obtain high sorbitol content fraction, maltitol syrup fraction (b) having a maltitol content of at least 97.5% by weight in the solid component and polyol fraction whose degree of polymerization (DP) is 3 or more;
4) the fourth step of concentrating said maltitol syrup fraction (b) and then spray-drying or kneading under cooling it in the presence of a seed crystal.

Thirdly a process for manufacturing crystalline maltitol and crystalline mixture solid containing the maltitol, characterized in that the process passes sequentially through the following steps;

1) the first step of hydrogenating syrup having a maltose content of 40 to 75% by weight in the solid component under the existence of catalyst to obtain corresponding syrup of sugar alcohol;
2) the second step of chromatographically separating said syrup of sugar alcohol by supplying said syrup of sugar alcohol to a column packed with a cation exchange resin to obtain high sorbitol content fraction, maltitol syrup fraction (a) having a maltitol content of 80.5 to 86.5% by weight in the solid component and polyol fraction whose degree of polymerization (DP) is 3 or more;
3) the third step of chromatographically separating said maltitol syrup fraction (a) by supplying said maltitol syrup fraction (a) to a column packed with a cation exchange resin to obtain high sorbitol content fraction, maltitol syrup fraction (b) having a maltitol content of 97.5% by weight or more in the solid component and polyol fraction whose degree of polymerization (DP) is 3 or more;
4) the fourth step having a sub-step of crystallizing, in the presence of a seed crystal, a part of the syrup resulting from a concentration of said maltitol syrup fraction (b) to separate crystalline maltitol from mother liquor having a maltitol content of 90% by weight or more in the solid component, and another sub-step of spray-drying or kneading under cooling, in the presence of a seed crystal, remaining part of the syrup resulting from a concentration of said maltitol syrup fraction(b) to obtain crystalline mixture solid containing crystalline maltitol.
5) the fifth step of spray-drying or kneading under cooling the mother liquor obtained in the fourth step in the presence of a seed crystal to obtain crystalline mixture solid containing crystalline maltitol.

Fourthly a process as defined in any of the first through the third above, wherein catalytic hydrogenation in the first step is conducted in a continuous process by using a Raney catalyst prepared by quenching molten nickel and aluminum and subjecting this material, in as-manufactured form or after milling, to classification and activation, or a Raney catalyst prepared by forming a powder thereof into pellets.

The maltose which is employed as the raw material in the present invention may be any material with a maltose content of 40 to 75% by weight in the solid component, such as one derived from potato starch, corn starch, tapioca starch, or the like. Maltose with relatively low oligosaccharide content manufactured using inexpensively procured starch as a raw material and enzymes facilitates implementation of the various steps of the present invention, and is favorable for use for this reason.

Maltose with a maltose content of less than 40% by weight in the solid component obtains an extremely small amount of maltitol fraction in chromatographic separation, and accordingly the productivity of the target crystalline maltitol and distalline mixture solid containing this declines.

Maltose with a maltose content exceeding 75% by weight in the solid component requires the use of expensive enzymes during its manufacture, and requires that liquefaction and saccharification of the starch be conducted at dilute concentrations; in particular, maltose above 95% by weight cannot be manufactured with an enzyme reaction alone, and must be passed through crystallization and chromatographic separation after liquefaction and saccharification. It is therefore difficult to manufacture or procure such products inexpensively, and they are unsuitable for use as raw materials for industrial processes.

The concentration of the maltose syrup used in catalytic hydrogenation in the first step is preferably 30 to 75% by weight.

When the concentration is below 30% by weight, the quantities which must be handled become quite large, as a result of which productivity is poor and the cost of concentration in subsequent steps is high.

When the concentration is above 75% by weight, in many cases, unreacted substance is produced during catalytic hydrogenation and the viscosity of the syrup becomes quite high, making separation of the syrup and the hydrogenation catalyst difficult.

Virtually any of the catalysts commonly used in catalytic hydrogenation of saccharides may be used as the catalyst in catalytic hydrogenation during the first step. Commercially available Raney nickel catalysts and noble metal catalysts can be used; lump form Raney catalysts prepared by quenching molten nickel and aluminum followed by activation are favorable for use, since they have high activity and withstand service for extended periods.

It is also possible to conduct catalytic hydrogenation by a batch process using a catalyst of powder form; on an industrial level, however, a continuous process employing a fixed bed packed with a catalyst produced by forming powder into pellets or lump foam catalyst prepared by quenching molten metal is favorable.

The parameters for conducting hydrogenation in the present invention may be any set designed such that no significant decomposition of the maltose and maltitol occurs. Ordinarily, it is favorable to conduct the reaction under a hydrogen pressure of 10 $kg/cm^2$ or above (preferably 50 to 200 $kg/cm^2$) and a temperature of 90 to 150° C.

The sugar alcohol syrup obtained in the first step can be subjected to a process to remove the catalyst, decolorized and deionized with activated carbon or an ion exchange resin, and concentrated to produce the required concentration, if necessary, before subjecting it to the second step.

Virtually any commercially available resin can be used as the cation exchange resin used in the second step of the present invention. The use of a strongly acidic cation exchange resin of a styrene-divinyl benzene cross-linked polymer to which sulfonic groups are bonded and which is charged with sodium ion or calcium ion is particularly favorable.

Chromatographic separation in the second step may be implemented in a batch type, pseudo-moving bed type, single column type, or multiple column type, and known methods may be used for the process. If the sorbitol content in the syrup of sugar alcohol applied to the chromatographic separation is low, a multiple column type/pseudo-moving bed type is favorable; if the amount of sorbitol fraction is quite large, a batch type is favorable.

The conditions in chromatographic separation are selected so that the maltitol-containing syrup fraction (a) obtained in the second step has a maltitol content of 80.5 to 86.5% by weight in the solid component. If the maltitol content is less than 80.5% by weight, productivity of the maltitol-containing syrup (b) in the third step declines.

If the maltitol content in the maltitol-containing syrup fraction (a) exceeds 86.5% by weight in the solid component, productivity of the maltitol-containing syrup(a) declines, with the result that productivity of crystalline maltitol and crystalline mixture solid containing this declines as well.

The maltitol-containing syrup (a) obtained in the second step is sent to the third step in as-manufactured form, or after concentration process if necessary.

Chromatographic separation in the third step may employ the same cation exchange resin and chromatographic separation configuration used in the second step. Since the maltitol-containing syrup (a) already has a low sorbitol content, a multiple column type/pseudo-moving bed type is favorable.

The conditions in chromatographic separation are selected so that the maltitol-containing syrup fraction (b) obtained in the third step has a maltitol content of 97.5% or more by weight in the solid component.

If the maltitol content in the solid component is less than 97.5% by weight, it becomes necessary to lower crystalline maltitol productivity in order to obtain a mother liquor having a maltitol content of 90% by weight or more in the solid component during crystallization in the fourth step, while conversely, attempting to raise the crystalline maltitol productivity will produce a mother liquor with a maltitol content below 90% by weight in the solid component. Accordingly, maltitol crystallization is extremely slow or does not proceed, even with kneading under cooling or spray drying in the presence of seed crystals, and such conditions are not useful for producing crystalline mixture solid containing maltitol.

The fraction with the high sorbitol content and the polyol fraction whose DP is 3 or more obtained in the second step and the third step may be used in as-manufactured form, in a combination of the fractions, or in combination with a sugar alcohol of any desired composition for use as a commercially available hydrogenated starch hydroysate or the like in various food products, pharmaceuticals, and cosmetics.

In the fourth step of the present invention, the maltitol-containing syrup (b) is concentrated and then crystallized and centrifuged to produce crystalline maltitol and a mother liquor with a maltitol content of 90% by weight or more in the solid component. The crystallization concentration is preferably held to within the range 60 to 90% by weight and the temperature within the range 10 to 60° C., selected such that the maltitol content in the solid component in the mother liquor so obtained is 90% by weight or more.

At this time, it is sufficient for crystallization that the maltitol content in the solid component in the mother liquor ultimately obtained is 90% by weight or more, and accordingly when crystalline maltitol is to be manufactured in large quantities, the production yield can be increased by conducting crystallization multiple times.

Under conditions such that the crystallization concentration exceeds 90% by weight or the temperature is below 10° C., the viscosity of the crystalline slurry will rise, making it difficult to separate the precipitated crystals and impossible to obtain a mother liquor with a maltitol content of 90% by weight or more in the solid component.

Conversely, if the crystallization concentration is below 60% by weight or the temperature is above 60° C., maltitol crystals do not precipitate or, even if they do precipitate, have a poor recovery rate.

The crystalline maltitol which precipitates in the fourth step is separated from the mother liquor by centrifugal separation, filter press or other means.

The separated mother liquor having a maltitol content of 90% by weight or more in the solid component is concentrated to a concentration of 80 to 99% by weight, and then spray dried or kneaded under cooling by a kneader or an extruder in the presence of seed crystal, solidified, dried, and crushed to produce crystalline mixture solid containing crystalline maltitol.

An example of a more specific method for producing crystalline mixture solid containing crystalline maltitol through kneading under cooling is the method disclosed in Japanese TOKKYO-KOKOKU-KOHO (Publication after Examination for Oposition) HEISEI 7(1995)-14953 (hereinafter referred to as TOKKOHEI 7-14953).

The maltitol-containing syrup (b) obtained in the third step of the present invention can be concentrated to a concentration of 80 to 99% by weight without crystallization and centrifugation, and then spray dried or kneaded under cooling by a kneader or an extruder in the presence of seed crystals, solidified, dried, and crushed to produce crystalline mixture solid containing crystalline maltitol.

The entire amount of maltitol-containing syrup (b) obtained in the third step of the present invention can be subjected to the crystallization process, or a portion or the entire amount thereof can be spray dried or kneaded under cooling by a kneader or an extruder in the presence of seed crystals, solidified, dried, and crushed to produce crystalline mixture solid containing crystalline maltitol.

As described above, through implementation of the present invention, it becomes possible to manufacture in high yield high-value added crystalline maltitol and crystalline mixture solid containing crystalline maltitol from raw materials which are inexpensively procured.

Implementing chromatographic separation in two stages makes it possible for the maltitol contained in the sugar alcohol syrup afforded by catalytic hydrogenation to be adequately separated from the sorbitol and the DP≧3 oligosaccharide. It also makes it possible for mother liquor produced when crystalline maltitol is manufactured in the fourth step to be spray dried or kneaded under cooling to produce crystalline mixture solid containing crystalline maltitol.

Implementing chromatographic separation in two stages also makes it possible to conduct the crystallization in two stages necessary to obtain crystalline maltitol while maintaining a maltitol purity sufficient for obtaining crystalline mixture solid containing crystalline maltitol within the mother liquor, thereby obtaining crystalline maltitol in large quantities.

After concentrating a portion or all of the maltitol-containing syrup fraction obtained in the third step, spray drying or kneading under cooling by a kneader or an extruder in the presence of seed crystals, solidifying, drying and crushing can be performed to produce crystalline mixture solid containing crystalline maltitol. Accordingly, the manufacturing balance of crystalline maltitol and crystalline mixture solid containing this can be selected freely in response to current market demand.

Through implementation of the present invention, the sorbitol fraction and DP≧3 oligosaccharide fraction obtained as by-products during the chromatographic separation step can be used in as-manufactured form, in a combination of the two fractions, or in combination with a sugar alcohol of any desired composition for use as a commercially available hydrogenated starch hydrolysate or the like in various food products, pharmaceuticals, and cosmetics.

By implementing the present invention, a syrup with a maltose content of 40 to 75% by weight in the solid component, an inexpensively procured product, can be used as a raw material for the production in the desired balance of high-value added crystalline maltitol and crystalline mixture solid containing this.

BRIEF DESCRIPTION OF THE DRAWINGS

FIG. 2 is a simplified illustration of the chromatographic separation apparatus used for first stage fractionation in the process of implementing the present invention; and FIG. 3 is a simplified illustration of the chromatographic separation apparatus used for second stage fractionation in the process of implementing the present invention.

Figure 1:
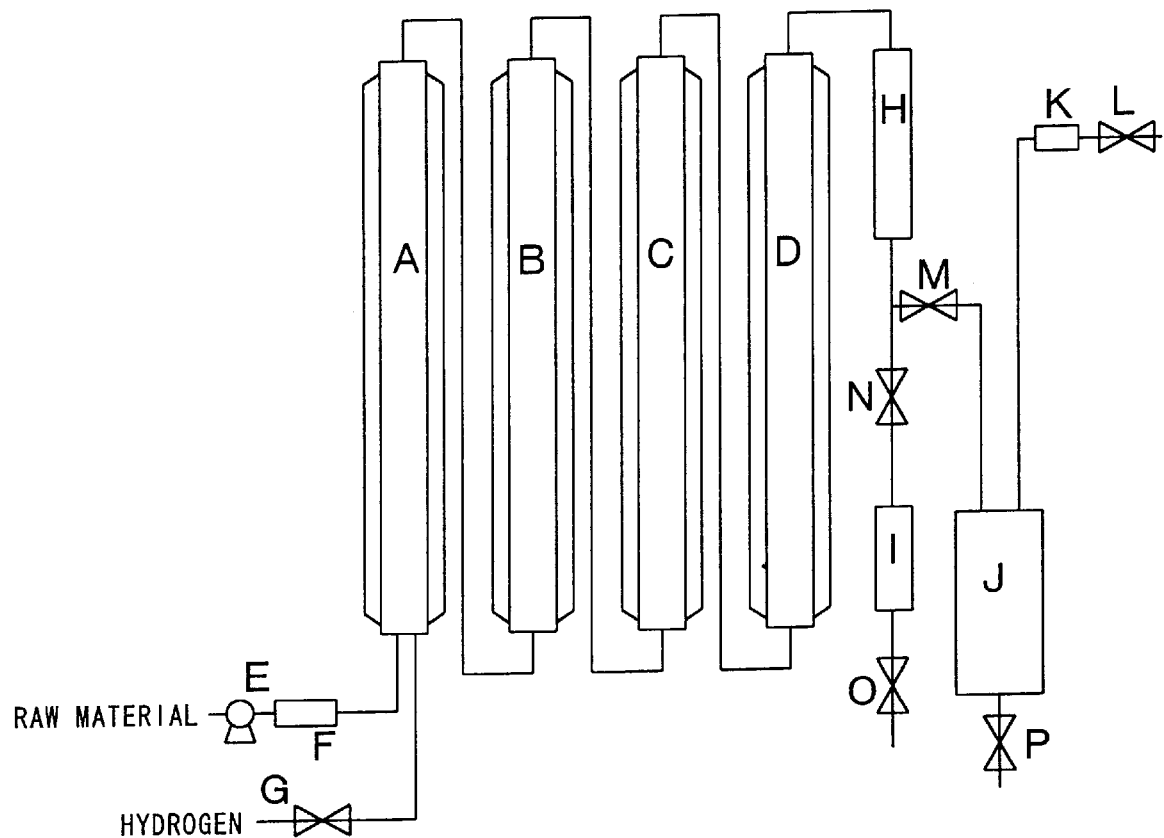
FIG. 1 is a simplified illustration of the catalytic hydrogenation apparatus used in implementing the present invention.

In the drawings, A indicates a column, E indicates a pump, F indicates a preheater, I indicates a sample pot, J indicates a trap pot, K indicates a flow meter, L indicates a control valve, and M indicates a valve.

BEST MODE FOR CARRYING OUT THE INVENTION

The method of the present invention will be described in further detail below through examples. However, the technical scope of the present invention is in no way limited to these examples.

In the following examples, % indicates % by weight unless indicated otherwise.

EXAMPLE 1

(Catalytic Hydrogenation Apparatus)

The catalytic hydrogenation apparatus in this example is equipped with four jacketed 5 liter stainless steel pressure resistant containers (inside diameter 6.6 cm; height 160 cm), indicated by columns A, B, C, and D, connected in series in the manner shown in FIG. 1. A raw material feed pump E is connected to the bottom of column A through a preheater F, and a sample pot I is connected to the top of column D through a cooler H. A trap pot J is also connected to the apparatus.

Hydrogen gas is introduced from the bottom of column A and exits from the top of column D. Separation from the liquid portion is performed in the trap pot J, after which the gas is blown into the atmosphere through a flow meter K and a control valve L.

Heated oil is circulated through the preheater F and the jackets of the columns A, B, C, and D to maintain the system at a given temperature.

The valve M is usually open and the valves N, O, and P are closed. The reaction liquid coming from the column D is trapped in the pot J and periodically discharged through valve P.

During sampling, valve M is closed, valve N is opened, and sample is discharged from the pot I through valve O.
(Preparation of Hydrogenation Catalyst)

60 kg nickel metal and 60 kg aluminum metal were heated and melted, and then quenched by dripping the melt through a nozzle onto a cooled water surface located 20 cm below.

The lump alloy so obtained was a mixture with a particle size of 1 to 15 mm.

This product was broken by a crusher and then sieved to produce 49.8 kg of quenched lump alloy with a particle size of 2 to 4 mm.

340 kg 10% NaOH aqueous solution was placed in a 500 liter heated, jacketed stainless steel container and heated to 50° C. 46 kg of the quenched lump alloy prepared earlier, contained in a stainless steel cage, was added thereto.

The temperature was raised to 60° C. and held there for 60 minutes. The cage was then withdrawn and rinsed.

The catalyst development rate so achieved was computed following the equation given below. The development rate was 20.3%.

development rate (%) =

(amount of eluted aluminum / aluminum content of alloy) × 100

(Catalytic Hydrogenation Reaction)

The developed catalyst was packed into the columns of the catalytic hydrogenation apparatus described above.

Next, the columns were heated to 140° C. A sugar solution with a sugar composition containing 1.6% glucose, 67.3% maltose, 13.2% maltotriose, and 17.9% DP≧4 polyol was prepared in 50% concentration and fed from the pump E at a rate of 10 liter/hr.

The hydrogen pressure was held at 150 kg/cm$^2$, and the hydrogen flow was adjusted to 85 liter/hr.

This hydrogenation reaction was operated continuously for three days.

The purity of 720 liter of discharged solution was analyzed using liquid chromatography. The composition of the hydrogenated liquid was found to be 1.8% sorbitol, 67.2% maltitol, 13.2% maltotriitol, 17.8% DP≧4 sugar alcohol, and 0.03% unreduced substance.

(First Stage Fractionation Apparatus)

As shown in FIG. 2, the first stage fractionation apparatus used in this example is equipped with jacketed 50 liter stainless steel columns (inside diameter 21 cm; length 150 cm), 2A through 2C, which are connected in series. A hydrogenated liquid feed pump 2D is connected to the top of column 2A through a preheater 2H and a shut-off valve 2E, as is a feed pump 2F through the preheater 2H and a shut-off valve 2G. Discharge liquid tanks 2I, 2J, 2K, and 2L are connected to the bottom of column 2C through change-over valves 2M, 2N, 2O, and 2P. The discharge liquid is sent from the bottom of column 2C through changeover valve 2M, 2N, 2O, or 2P to discharge liquid tank 2I, 2J, 2K, or 2L. The columns 2A through 2C are packed with 150 liter calcium-type strongly acidic ion exchange resin (manufactured by Japan Organo Co., Ltd.; sulfonic type CG6010).

(First Stage Fractionation)

While holding the columns 2A, 2B, and 2C at 60° C., valves 2E and 2P were opened and 2G, 2M, 2N, and 2O were closed.

After purifying the aforementioned hydrogenated liquid with the ion exchange resin following common methods, it was concentrated to 60% concentration. 45 kg thereof was fed through pump 2D at a rate of 2.6 liter/min.

Next, valve 2E was closed, valve 2G was opened, and water was fed at a rate of 2.6 liter/min by the feed pump 2F for 40 minutes. This procedure was repeated.

When the sugar concentration of the discharge liquid on the valve 2P side reached 0.2%, the valve 2P was closed and the valve 2O was opened. After 18 minutes, the valve 2O was closed and 2N was opened. After another 30 minutes, the valve 2N was closed and 2M was opened. After another 24 minutes, the valve 2M was closed and 2P was opened. This procedure was repeated on the discharge side.

The weight, concentration, and sugar composition of the discharge liquid which collected in tanks 2K, 2J, and 2I are given in Table 1.

TABLE 1

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Tank 2K | 18.0 | 520.0 | 93.6 | 0.2 | 15.9 | 19.5 | 64.4 |
| Tank 2J | 29.2 | 967.8 | 282.6 | 1.1 | 83.4 | 11.8 | 3.7 |
| Tank 2I | 3.6 | 700.0 | 25.2 | 16.0 | 78.5 | 4.7 | 0.8 |

(Second Stage Fractionation Apparatus)

As shown in FIG. 3, the second stage fractionation apparatus used in this example is equipped with ten jacketed 10 liter stainless steel columns (inside diameter 9.6 cm; length 150 cm), 3A through 3J, which are connected in series. A hydrogenated liquid feed pump 3K is connected to the top of column 3A through a preheater 3O and a shut-off valve 3L, as is a feed pump 3M through the preheater 3O and a shut-off valve 3N. Discharge liquid tanks 3Q and 3R are connected to the bottom of column 3J through a changeover valve 3P. The discharge liquid is sent from the bottom of column 3J through change-over valve 3P to discharge liquid tank 3Q or 3R.

The columns 3A through 3J are packed with 100 liter calcium-type strongly acidic ion exchange resin (manufactured by Japan Organo Co., Ltd.; sulfonic type CG6010).

(Second Stage Fractionation)

While holding the columns 3A through 3J at 60° C., valve 3L was opened, valve 3N was closed, and the change-over valve 3P was opened to the discharge liquid tank 3R side.

12 kg of maltitol-containing solution prepared by adjusting the discharge liquid in the first stage fraction tank 2J to 60% concentration was fed through pump 3K at a rate of 50 liter/hr.

Next, valve 3L was closed, valve 3N was opened, and water was fed at a rate of 50 liter/hr by the feed pump 3M for 160 minutes. This operation was repeated.

When the maltitol purity of the discharge liquid on the tank 3R side reached 97.5%, the change-over valve 3P was switched to the tank 3Q side. When the maltitol purity subsequently reached 97.5% or below, the change-over valve 3P was switched to the tank 3R side. This procedure was repeated on the discharge side.

The weight, concentration, and sugar composition of the discharge liquid in tank 3Q and the discharge liquid in tank 3R are given in Table 2.

TABLE 2

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Tank 3Q | 6.9 | 2437.7 | 168.2 | 0.2 | 98.2 | 1.3 | 0.3 |
| Tank 3R | 3.9 | 2438.5 | 95.1 | 2.7 | 57.4 | 30.2 | 9.7 |

(Manufacture of Crystalline Maltitol)

205 kg maltitol solution prepared by purifying the discharge liquid in the aforementioned tank 3Q using an ion exchange resin and then concentrating it to 78% concentration was placed in a jacketed 200 liter-capacity crystallization vessel equipped with an agitator. At 55° C., crystalline maltitol powder was added as seeds in an amount of 0.1% with respect to the solids content of the maltitol solution, which was then slowly cooled to 20° C. over 24 hours under slow agitation.

The slurry so obtained was centrifuged in a centrifugal separator. The crystals were washed in a small quantity of water to produce crystalline maltitol and a mother liquor. Results are presented in Table 3.

TABLE 3

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Crystalline maltitol | 96.2 | 86.4 | 83.1 | 0 | 99.7 | 0.2 | 0.1 |
| Mother liquor | 63.3 | 107.1 | 67.8 | 0.4 | 96.3 | 2.7 | 0.6 |

(Manufacture of Crystalline mixture solid Containing Crystalline Maltitol)

The above mother liquor obtained during crystalline maltitol manufacture was concentrated to 95% concentration and then supplied at a rate of 22 kg/hr into a food product-use twin-screw extruder (TEX38FSS-20AW-V, manufactured by Nihon Seikosho K. K.) whose temperature had been adjusted to approximately 100° C. A crystalline mixture solid powder containing crystalline maltitol (95.3% maltitol purity) was added as seeds in an amount of approximately 30% with respect to the solids content of the mother liquor. While kneading at 60 rpm, after two minutes, the product was cooled to 40° C. by the time of discharge from the extruder. Maltitol magma was discharged from an extrusion nozzle with twelve 4 mm-diamter holes. The operating time was 2.5 hours.

The maltitol magma was cooled, dried, and pulverized, yielding 66.2 kg crystalline mixture solid containing crystalline maltitol. The maltitol purity of this product was 96.0%.

EXAMPLE 2

(Catalytic Hydrogenation Reaction)

A starting material comprising a sugar solution with a composition containing 1.1% glucose, 49.1% maltose, 11.6% maltotriose, and 38.2% DP≧24 polyol was prepared in 50% concentration. Using the catalytic hydrogenation apparatus of Example 1, this was fed from the pump E at a rate of 8 liter/hr. The hydrogen pressure was held at 150 kg/cm$^2$, and the hydrogen flow was adjusted to 85 liter/hr. Hydrogenation reaction was operated continuously for six days.

The composition of the discharge liquid was found to be 1.3% sorbitol, 49.0% maltitol, 11.5% maltotriitol, and 38.2% DP≧4 sugar alcohol.

(First Stage Fractionation)

Using the fractionation apparatus shown in FIG. 2, first stage fractionation was conducted under the same conditions as in Example 1, with the exception that the valve 2O open time was 24 minutes and the valve 2N open time was 24 minutes.

The weight, concentration, and sugar composition of the discharge liquid which collected in tanks 2K, 2J, and 2I are given in Table 4.

TABLE 4

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Tank 2K | 33.7 | 1036.2 | 439.2 | 0.1 | 29.5 | 12.5 | 57.9 |
| Tank 2J | 19.2 | 985.9 | 179.3 | 1.6 | 81.2 | 10.4 | 6.8 |
| Tank 2I | 2.7 | 974.1 | 26.3 | 15.5 | 76.7 | 5.5 | 2.3 |

(Second Stage Fractionation)

Using the discharge liquid in tank 2J as the raw material and using the fractionation apparatus shown in FIG. 3, second stage fractionation was conducted under the same conditions as in Example 1, with the exception that the maltitol purity was 96.0% when the tank for the discharged sugar solution was changed to the tank 3Q side.

The weight, concentration, and sugar composition of the discharge liquid in tank 3Q and the discharge liquid in tank 3R are given in Table 5.

TABLE 5

|  | Concentration | Weight | Solids weight | Sugar alcohol composition (%) | | | |
|---|---|---|---|---|---|---|---|
|  | (%) | (kg) | (kg) | Sorbitol | Maltitol | Maltotriitol | DP ≧ 4 |
| Tank 3Q | 8.9 | 1334.8 | 118.8 | 0.3 | 97.8 | 1.3 | 0.6 |
| Tank 3R | 4.5 | 1337.8 | 60.2 | 4.2 | 48.4 | 28.4 | 19.0 |

(Manufacture of Crystalline Maltitol)

150 kg maltitol solution prepared by purifying the discharge liquid in the aforementioned tank 3Q using an ion exchange resin and then concentrating it to 78% concentration was placed in a jacketed 120 liter-capacity crystallization vessel equipped with an agitator. At 55° C., crystalline maltitol powder was added as seeds in an amount of 0.1% with respect to the solids content of the maltitol solution, which was then slowly cooled to 20° C. over 24 hours under slow agitation.

The slurry so obtained was centrifuged in a centrifugal separator. The crystals were washed in a small quantity of water to produce crystalline maltitol (A) and mother liquor (A).

This mother liquor (A) was concentrated to 78% concentration, and 60 liter of it was placed in a crystallization vessel. At 55° C., crystalline maltitol powder was added as seeds in an amount of 0.1% with respect to the solids content of the mother liquor (A), which was then slowly cooled to 20° C. over 24 hours. The slurry so obtained was centrifuged in a centrifugal separator. The crystals were washed in a small quantity of water to produce crystalline maltitol (B) and mother liquor (B).

The weight and sugar composition of the crystalline maltitol (A), mother liquor (A), crystalline maltitol (B), and mother liquor (B) are given in Table 6.

tured under the same conditions as in Example 1, with the exception that the purity of the crystalline mixture solid powder containing crystalline maltitol which was used as seeds was 95.3%, and the operating time was 1.5 hours.

26.5 kg crystalline mixture solid of which the purity was 93.5% was obtained.

EXAMPLE 3

(Catalytic Hydrogenation Reaction)

40 kg 50% sugar solution with a sugar composition containing 1.0% glucose, 57.7% maltose, 12.7% maltotriose, and 28.6% DP≧24 polyol and 2 kg commercially available powdered Raney nickel catalyst (R-239, manufactured by Nikko Rica Corporation) were placed in a 50 liter stainless steel autoclave equipped with an electromagnetic agitator. A reaction was carried out for 120 minutes at a hydrogen pressure of 150 kg/cm$^2$ and a temperature of 130° C.

When the reaction was complete, the catalyst was filtered out from the hydrogenated liquid, which was then purified by common methods using a ion exchange resin.

The hydrogenation reaction was conducted in 20 batches to obtain 650 kg hydrogenated liquid of 60% concentration.

The composition of the hydrogenated liquid was found to be 1.2% sorbitol, 57.6% maltitol, 12.6% maltotriitol, and 28.6% DP≧4 sugar alcohol.

(First Stage Fractionation)

While holding the columns 2A through 2C at 60° C., valves 2E and 2P were opened, and 2G, 2M, 2N, and 2O were closed.

45 kg of the aforementioned hydrogenated liquid of 60% concentration was fed through pump 2D at a rate of 2.6 liter/min.

Next, valve 2E was closed, valve 2G was opened, and water was fed at a rate of 2.6 liter/min by the feed pump 2F for 40 minutes. This operation was repeated.

At another 7 minutes after the sugar concentration of the discharge liquid on the valve 2P side reached 0.2%, the valve

TABLE 6

|  | Concentration | Weight | Solids weight | Sugar alcohol composition (%) | | | |
|---|---|---|---|---|---|---|---|
|  | (%) | (kg) | (kg) | Sorbitol | Maltitol | Maltotriitol | DP ≧ 4 |
| Crystalline maltitol (A) | 99.5 | 61.5 | 58.5 | 0.1 | 99.6 | 0.2 | 0.1 |
| Mother liquor (A) | 66.1 | 88.5 | 58.5 | 0.5 | 96.0 | 2.3 | 1.1 |
| Crystalline maltitol (B) | 95.5 | 26.2 | 26.1 | 0.1 | 99.5 | 0.2 | 0.2 |
| Mother liquor (B) | 67.6 | 47.3 | 32.0 | 0.8 | 93.1 | 4.2 | 1.9 |

(Manufacture of Crystalline Mixture Solid containing Crystalline Maltitol)

Using mother liquor (B) as the raw material, crystalline mixture solid containing crystalline maltitol were manufac- 2P was closed and the valve 2O was opened. After 15 minutes, the valve 2O was closed and 2N was opened. After another 20 minutes, the valve 2N was closed and 2M was opened. After another 7 minutes, the valve 2M was closed and 2P was opened. This procedure was repeated on the discharge side.

The weight, concentration, and sugar composition of the discharge liquid which collected in tanks 2L, 2K, 2J, and 2I when 325 kg 60% hydrogenated liquid was processed using the procedure described above are given in Table 7.

TABLE 7

|  | Concentration | Weight | Solids weight | Sugar alcohol composition (%) | | | |
|---|---|---|---|---|---|---|---|
|  | (%) | (kg) | (kg) | Sorbitol | Maltitol | Maltotriitol | DP ≧ 4 |
| Tank 2L | 20.5 | 142.9 | 29.3 | 0 | 5.2 | 10.1 | 84.7 |
| Tank 2K | 37.9 | 235.4 | 89.2 | 0 | 54.0 | 16.4 | 29.6 |
| Tank 2J | 20.7 | 272.0 | 56.3 | 0.9 | 86.1 | 9.1 | 3.9 |
| Tank 2I | 3.1 | 400.0 | 12.4 | 13.6 | 75.2 | 7.5 | 3.7 |

(Second Stage Fractionation)

While holding the columns 3A through 3J at 60° C., valve 3L was opened, valve 3N was closed, and the change-over valve 3P was opened to the discharge liquid tank 3R side.

8 kg of maltitol-containing solution prepared by adjusting the discharge liquid in the first stage fraction tank 2J to 60% concentration was fed through pump 3K at a rate of 30 liter/hr.

Next, valve 3L was closed, valve 3N was opened, and water was fed at a rate of 30 liter/hr by the feed pump 3M for 260 minutes. This operation was repeated.

When the maltitol purity of the discharge liquid on the tank 3R side reached 98.8% or above, the change-over valve 3P was switched to the tank 3Q side. When the maltitol purity subsequently reached 98.8% or below, the change-over valve 3P was switched to the tank 3R side. This procedure was repeated on the discharge side.

The weight, concentration, and sugar composition of the discharge liquid in tank 3Q and the discharge liquid in tank 3R are given in Table 8.

TABLE 8

|  | Concentration | Weight | Solids weight | Sugar alcohol composition (%) | | | |
|---|---|---|---|---|---|---|---|
|  | (%) | (kg) | (kg) | Sorbitol | Maltitol | Maltotriitol | DP ≧ 4 |
| Tank 3Q | 6.8 | 501.5 | 34.1 | 0.1 | 99.2 | 0.5 | 0.2 |
| Tank 3R | 1.9 | 947.4 | 18.0 | 2.5 | 61.8 | 25.0 | 10.7 |

(Manufacture of Crystalline mixture solid Containing Crystalline Maltitol)

The discharge liquid in tank 3Q was purified by common methods using an ion exchange resin and then concentrated to 95% concentration. This product was supplied at a rate of 22 kg/hr into a food product-use twin-screw extruder (TEX38FSS-20AW, manufactured by Nihon Seikosho K. K.) whose temperature had been adjusted to approximately 100° C. A crystalline maltitol powder (99.0% maltitol content) was added as seeds in an amount of approximately 30% with respect to the solids content. While kneading at 60 rpm, after two minutes, the product was cooled to 40° C. by the time of discharge from the extruder. Maltitol magma was discharged from an extrusion nozzle with twelve 4 mm-diamter holes. The operating time was 1.5 hours.

The maltitol magma was cooled, dried, and pulverized to obtain 26.5 kg crystalline mixture solid containing crystalline maltitol. The maltitol purity of this product was 99.1%.

(Manufacture of Oligosaccharide Alcohol)

The discharge liquid in tank 2L and the discharge liquid in tank 3R were each purified by common methods using an ion exchange resin and then concentrated to 70% concentration. These were designated as tank 2L concentrated discharge liquid and tank 3R concentrated discharge liquid.

30 kg of the tank 2L concentrated discharge liquid, 4 kg of the tank 3R concentrated discharge liquid, and 1 kg commercially available 70% D-sorbitol aqueous solution (manufactured by Towa Chemical Industry Co., Ltd.; 99.3% purity) were mixed. The sugar composition of the mixed oligosaccharide alcohol was 3.1% sorbitol, 11.5% maltitol, 11.5% maltotriitol, and 73.8% DP≧4 sugar alcohol.

The sweetness was 15% of that of sucrose and the viscosity was 3650 cp (25° C).

A commercially available starch hydrolysate liquid M-20 (manufactured by Nihon Shokuhin Kako Co., Ltd.) in 50% aqueous solution (1.4 kg) was reacted for 120 minutes in the presence of 10 g powdered Raney nickel catalyst R-239 (manufactured by Nikko Rica Corporation) in a 2.4 liter autoclave at 130° C., 150 kg/cm$^2$ hydrogen pressure. The catalyst was then filtered out, the product was purified with an ion exchange resin, and then concentrated to produce a product comparable to Hydrogenated Starch Hydrolysate PO-20 (trade name of Towa Chemical Industry Co., Ltd.)

The composition of this product was 2.6% sorbitol, 10.0% maltitol, 10.8% maltotriitol, and 76.6% DP≧4 sugar alcohol, virtually the same composition as the mixed oligosaccharide alcohol prepared earlier. The viscosity and sweetness were also comparable.

EXAMPLE 4

(Catalytic Hydrogenation Reaction)

A raw material comprising a sugar solution with a composition containing 1.2% glucose, 74.2% maltose, 13.7% maltotriose, and 10.9% DP≧4 polyol was prepared in 50% concentration. Using the catalytic hydrogenation apparatus of Example 1, this was fed from the pump E at a rate of 10 liter/hr. The hydrogen pressure was held at 150 kg/cm$^2$, and the hydrogen flow was adjusted to 85 liter/hr. This hydrogenation reaction was operated continuously for two days to obtain 480 liter of discharge liquid.

The composition of the discharge liquid was found to be 1.4% sorbitol, 74.1% maltitol, 13.6% maltotriitol, and 10.9% DP$\geq$4 sugar alcohol.

(First Stage Fractionation)

First stage fractionation was conducted by the same method as in Example 1, with the exception that the valve 2O open time was 13 minutes, the valve 2N open time was 39 minutes, and the valve 2M open time was 20 minutes.

The weight, concentration, and sugar composition of the discharge liquid which collected in tanks 2K, 2J, and 2I are given in Table 9.

described under "Manufacture of Crystalline Mixture Solid Containing Crystalline Maltitol" in Example 1 was then followed, with the exception that a crystalline mixture solid powder containing crystalline maltitol with 97.5% maltitol purity was used as the seeds. The operating time was 2 hours. The operation yielded 52.6 kg crystalline mixture solid containing crystalline maltitol with 97.7% maltitol purity.

(Manufacture of Oligosaccharide Alcohol)

The discharge liquid in tank 2K and the discharge liquid in tank 3R were each purified by common methods using an ion exchange resin and then concentrated to 70% concentration. These were designated as tank 2K concentrated discharge liquid and tank 3R concentrated discharge liquid.

TABLE 9

| | Concentration (%) | Weight (kg) | Solids weight (kg) | Sugar alcohol composition (%) | | | |
|---|---|---|---|---|---|---|---|
| | | | | Sorbitol | Maltitol | Maltotriitol | DP $\geq$ 4 |
| Tank 2K | 27.0 | 223.7 | 60.4 | 0.1 | 47.4 | 22.3 | 30.2 |
| Tank 2J | 21.9 | 670.3 | 146.8 | 0.9 | 85.2 | 10.4 | 3.5 |
| Tank 2I | 2.5 | 304.0 | 7.6 | 21.2 | 71.3 | 6.5 | 1.0 |

(Second Stage Fractionation)

While holding the columns 3A through 3J at 60° C., valve 3L was opened, valve 3N was closed, and the change-over valve 3P was opened to the discharge liquid tank 3R side.

8 kg of maltitol-containing solution prepared by adjusting the discharge liquid in the first stage fraction tank 2J to 60% concentration was fed through pump 3L at a rate of 30 liter/hr.

Next, valve 3L was closed, valve 3N was opened, and water was fed at a rate of 30 liter/hr by the feed pump 3M for 260 minutes. This operation was repeated.

When the maltitol purity of the discharge liquid on the tank 3R side reached 96.7% or above, the change-over valve 3P was switched to the tank 3Q side. When the maltitol purity of the discharge liquid subsequently reached 96.7% or below, the change-over valve 3P was switched to the tank 3R side. This procedure was repeated on the discharge side.

The weight, concentration, and sugar composition of the discharge liquid in tank 3Q and the discharge liquid in tank 3R are given in Table 10.

22 kg of the tank 2K concentrated discharge liquid, 10 kg of the tank 3R concentrated discharge liquid, and 0.43 kg 70% D-sorbitol aqueous solution (99.3% purity) were mixed.

The sugar composition of the mixed oligosaccharide alcohol was 2.1% sorbitol, 50.5% maltitol, 23.9% maltotriitol, and 23.5% DP$\geq$4 sugar alcohol.

The sweetness was 35% of that of sucrose and the viscosity was 320 cp (25° C.).

A commercially available starch hydrolysate liquid M-40 (manufactured by Nihon Shokuhin Kako Co., Ltd.) in 50% aqueous solution (1.4 kg) was reacted for 120 minutes in the presence of 10 g powdered Raney nickel catalyst R-239 (manufactured by Nikko Rica Corporation) in a 2.4 liter autoclave at 130° C., 150 kg/cm$^2$ hydrogen pressure. The catalyst was then filtered out, the product was purified with an ion exchange resin, and then concentrated to 70% concentration to produce a product comparable to hydrogenated starch hydrolysate PO-40 (trade name of Towa Chemical Industry Co., Ltd.).

TABLE 10

| | Concentration (%) | Weight (kg) | Solids weight (kg) | Sugar alcohol composition (%) | | | |
|---|---|---|---|---|---|---|---|
| | | | | Sorbitol | Maltitol | Maltotriitol | DP $\geq$ 4 |
| Tank 3Q | 13.8 | 626.1 | 86.4 | 0.2 | 97.8 | 1.6 | 0.4 |
| Tank 3R | 7.1 | 595.7 | 42.3 | 2.7 | 59.5 | 28.4 | 9.8 |

(Manufacture of Crystalline Mixture Solid Containing Crystalline Maltitol)

The discharge liquid in tank 3Q was purified by common methods using an ion exchange resin. The procedure The composition of this product was 2.3% sorbitol, 50.9% maltitol, 23.4% maltotriitol, and 23.4% DP$\geq$4 sugar alcohol, virtually the same composition as the mixed oligosaccharide alcohol prepared earlier. The viscosity and sweetness were also comparable.

EXAMPLE 5
(Catalytic Hydrogenation Reaction)

40 kg 50% sugar solution with a sugar composition containing 0.9% glucose, 62.4% maltose, 12.3% maltotriose, and 24.4% DP$\geq$4 polyol and 2 kg commercially available powdered Raney nickel catalyst (R-239, manufactured by Nikko Rica Corporation) were placed in a 50 liter stainless steel autoclave equipped with an electromagnetic agitator. A reaction was carried out for 120 minutes at a hydrogen pressure of 150 kg/cm$^2$ and a temperature of 130° C.

When the reaction was complete, the catalyst was filtered out from the hydrogenated liquid, which was then purified by common methods using a ion exchange resin.

The hydrogenation reaction was conducted in 34 batches to obtain 1100 kg hydrogenated liquid of 60% concentration.

The composition of the hydrogenated liquid was found to be 1.1% sorbitol, 62.3% maltitol, 12.2% maltotriitol, and 24.4% DP$\geq$4 sugar alcohol.

(First Stage Fractionation)

First stage fractionation was conducted by the same method as in Example 1, with the exception that the valve 2O open time was 18 minutes, the valve 2N open time was 34 minutes, and the valve 2M open time was 20 minutes.

The weight, concentration, and sugar composition of the discharge liquid which collected in tanks 2K, 2J, and 2I are given in Table 11.

TABLE 11

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP $\geq$ 4 |
| Tank 2K | 36.2 | 925.7 | 335.1 | 0 | 43.6 | 15.2 | 41.2 |
| Tank 2J | 16.4 | 1627.9 | 267.0 | 1.1 | 85.7 | 8.8 | 4.4 |
| Tank 2I | 2.1 | 906.2 | 19.0 | 19.7 | 70.8 | 6.8 | 2.7 |

(Second Stage Fractionation)

While holding the columns 3A through 3J at 60° C., valve 3L was opened, valve 3N was closed, and the change-over valve 3P was opened to the discharge liquid tank 3R side.

12 kg of maltitol-containing solution prepared by adjusting the discharge liquid in the first stage fraction tank 2J to 60% concentration was fed through pump 3K at a rate of 50 liter/hr.

Next, valve 3L was closed, valve 3N was opened, and water was fed at a rate of 30 liter/hr by the feed pump 3M for 160 minutes. This operation was repeated.

When the maltitol purity of the discharge liquid on the tank 3R side reached 97.5% or above, the change-over valve 3P was switched to the tank 3Q side. When the maltitol purity of the discharge liquid subsequently reached 97.5% or below, the change-over valve 3P was switched to the tank 3R side. This procedure was repeated on the discharge side.

The weight, concentration, and sugar composition of the discharge liquid in tank 3Q and the discharge liquid in tank 3R are given in Table 12.

TABLE 12

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP $\geq$ 4 |
| Tank 3Q | 8.3 | 1840.9 | 152.8 | 0.2 | 98.3 | 1.2 | 0.3 |
| Tank 3R | 2.5 | 1770.6 | 44.3 | 4.2 | 42.8 | 34.6 | 18.4 |

(Manufacture of Crystalline Mixture Solid Containing Crystalline Maltitol--1)

A portion of the aforementioned discharge liquid in tank 3Q was purified by common methods using an ion exchange resin, and then concentrated to 95% concentration. The procedure described under "Manufacture of Crystalline Mixture Solid Containing Crystalline Maltitol" in Example 1 was then followed, with the exception that a crystalline maltitol powder (99.9% maltitol content) was used as the seeds to obtain 40 kg crystalline mixture solid containing crystalline maltitol. The maltitol purity of this product was 98.4%.

(Manufacture of Crystalline Maltitol)

134 kg sugar solution obtained by purifying the remainder of the discharge liquid in the aforementioned tank 3Q and then concentrating it to 75% concentration was placed in a jacketed 120 liter-capacity crystallization vessel equipped with an agitator. At 53° C., crystalline maltitol powder was added as seeds in an amount of 0.1% with respect to the solids content of the sugar solution, which was then slowly cooled to 20° C. over 24 hours under slow agitation.

The slurry so obtained was centrifuged in a centrifugal separator. The crystals were washed in a small quantity of water to produce the crystalline maltitol and mother liquor described in Table 13.

TABLE 13

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Crystalline maltitol | 95.6 | 47.1 | 45.0 | 0 | 99.9 | 0.1 | 0 |
| Mother liquor | 63.8 | 86.4 | 55.1 | 0.4 | 97.0 | 2.1 | 0.5 |

(Manufacture of Crystalline Mixture Solid Containing Crystalline Maltitol--2)

The aforementioned mother liquor was concentrated to 95% concentration. The procedure described under "Manufacture of Crystalline Mixture Solid Containing Crystalline Maltitol" in Example 1 was then followed, with the exception that a crystalline maltitol powder (99.0% maltitol purity) was used as the seeds to obtain 67 kg crystalline mixture solid containing crystalline maltitol. The maltitol purity of this product was 97.4%.

REFERENCE EXAMPLE (Fractionation)

The remainder of the 60%-concentration hydrogenated liquid obtained in catalytic hydrogenation in Example 3 was fractionated using the chromatographic separation apparatus described in FIG. 3.

While holding the columns 3A through 3J at 60° C., valve 3L was opened, valve 3N was closed, and the change-over valve 3P was opened to the discharge liquid tank 3R side.

8 kg of hydrogenated liquid was fed through pump 3K at a rate of 30 liter/hr.

Next, valve 3L was closed, valve 3N was opened, and water was fed at a rate of 30 liter/hr by the feed pump 3M for 260 minutes. This operation was repeated.

When the maltitol purity of the discharged sugar solution on the tank 3R side reached 98.8% or above, the change-over valve 3P was switched to the tank 3Q side. When the maltitol purity of the discharge liquid subsequently reached 98.8% or below, the change-over valve 3P was switched to the tank 3R side. This procedure was repeated on the discharge side.

This operation was repeated eleven times on both the charge side and the discharge side to treat 88 kg hydrogenated liquid (52.8 kg solids).

The weight, concentration, and sugar composition of the discharge liquid in tank 3Q and the discharge liquid in tank 3R are given in Table 14. The yield of discharge liquid with a high maltitol content was extremely small, only 4.2% on a solids conversion basis.

TABLE 14

|  | Concentration (%) | Weight (kg) | Solids weight (kg) | Sugar alcohol composition (%) | | | |
|---|---|---|---|---|---|---|---|
|  |  |  |  | Sorbitol | Maltitol | Maltotriitol | DP ≧ 4 |
| Tank 3Q | 2.8 | 78.6 | 2.2 | 0.1 | 99.2 | 0.5 | 0.2 |
| Tank 3R | 3.7 | 1362.2 | 50.4 | 1.2 | 55.8 | 13.2 | 29.8 |

We claim:

1. A process for manufacturing crystalline maltitol and crystalline mixture solid containing the maltitol, comprising the following sequential steps:

1) hydrogenating a syrup having a maltose content of 40 to 75% by weight of solids in the presence of a catalyst to obtain a corresponding syrup of sugar alcohol;

2) chromatographically separating said syrup of sugar alcohol by supplying said syrup of sugar alcohol to a column packed with a cation exchange resin to obtain a high sorbitol content fraction, a maltitol syrup fraction (a) having a maltitol content of 80.5 to 86.5% by weight of solids and a polyol fraction whose degree of polymerization (DP) is 3 or more;

3) chromatographically separating said maltitol syrup fraction (a) by supplying said maltitol syrup fraction (a) to a column packed with a cation exchange resin to obtain a high sorbitol content fraction, a maltitol syrup fraction (b) having a maltitol content of 97.5% by weight or more of solids and a polyol fraction whose degree of polymerization (DP) is 3 or more;

4) separating crystalline maltitol and a mother liquor having a maltitol content of 90% by weight or more solids by crystallizing after concentrating said maltitol syrup fraction (b); and 5) spray-drying or kneading under cooling the mother liquor obtained in the fourth step in the presence of a seed crystal to obtain a crystalline mixture solid containing crystalline maltitol.

2. A process as defined in claims 1, wherein catalytic hydrogenation in the first step is conducted in a continuous process by using a Raney catalyst prepared by quenching molten nickel and aluminum and subjecting this material, in as-manufactured form or after milling, to classification and activation, or a Raney catalyst prepared by forming a powder thereof into pellets.

3. A process for manufacturing crystalline maltitol and crystalline mixture solid containing the maltitol, comprising the following sequential steps:

1) hydrogenating syrup having a maltose content of 40 to 75% by weight of solids in the presence of a catalyst to obtain a corresponding syrup of sugar alcohol;

2) chromatographically separating said syrup of sugar alcohol by supplying said syrup of sugar alcohol to a column packed with a cation exchange resin to obtain a high sorbitol content fraction, a maltitol syrup fraction (a) having a maltitol content of 80.5 to 86.5% by weight of solids and a polyol fraction whose degree of polymerization (DP) is 3 or more;

3) chromatographically separating said maltitol syrup fraction (a) by supplying said maltitol syrup fraction (a) to a column packed with a cation exchange resin to obtain a high sorbitol content fraction, a maltitol syrup fraction (b) having a maltitol content of at least 97.5% by weight of solids and a polyol fraction whose degree of polymerization (DP) is 3 or more; and 4) concentrating said maltitol syrup fraction (b) and then spray-drying or kneading under cooling in the presence of a seed crystal.

4. A process as defined in claim 3, wherein catalytic hydrogenation in the first step is conducted in a continuous process by using a Raney catalyst prepared by quenching molten nickel and aluminum and subjecting this material, in as-manufactured form or after milling, to classification and activation, or a Raney catalyst prepared by forming a powder thereof into pellets.

5. A process for manufacturing crystalline maltitol and crystalline mixture solid containing the maltitol, comprising the following sequential steps;

1) hydrogenating a syrup having a maltose content of 40 to 75% by weight of solids in the presence of a catalyst to obtain a corresponding syrup of sugar alcohol;

2) chromatographically separating said syrup of sugar alcohol by supplying said syrup of sugar alcohol to a column packed with a cation exchange resin to obtain a high sorbitol content fraction, a maltitol syrup fraction (a) having a maltitol content of 80.5 to 86.5% by weight of solids and a polyol fraction whose degree of polymerization (DP) is 3 or more;

3) chromatographically separating said maltitol syrup fraction (a) by supplying said maltitol syrup fraction (a) to a column packed with a cation exchange resin to obtain a high sorbitol content fraction, a maltitol syrup fraction (b) having a maltitol content of 97.5% by weight or more of solids and a polyol fraction whose degree of polymerization (DP) is 3 or more;

4) a first sub-step of crystallizing, in the presence of a seed crystal, a part of the syrup resulting from concentration of said maltitol syrup fraction (b) to separate crystalline maltitol and mother liquor having a maltitol content of 90% by weight or more of solids, and a second sub-step of spray-drying or kneading under cooling, in the presence of a seed crystal, a remaining part of the syrup resulting from a concentration of said maltitol syrup fraction (b) to obtain a crystalline mixture solid containing crystalline maltitol; and 5) spray-drying or kneading under cooling the mother liquor obtained in the fourth step in the presence of a seed crystal to obtain a crystalline mixture solid containing crystalline maltitol.

6. A process as defined in claim 5, wherein catalytic hydrogenation in the first step is conducted in a continuous process by using a Raney catalyst prepared by quenching molten nickel and aluminum and subjecting this material, in as-manufactured form or after milling, to classification and activation, or a Raney catalyst prepared by forming a powder thereof into pellets.

* * * * *